US00PP13546P2

(12) United States Plant Patent
Ackerman et al.

(10) Patent No.: US PP13,546 P2
(45) Date of Patent: Feb. 4, 2003

(54) STRAWBERRY PLANT NAMED 'PS-2299'

(75) Inventors: Stephen M. Ackerman, Salinas, CA (US); Steven D. Nelson, Watsonville, CA (US); Michael D. Nelson, Watsonville, CA (US)

(73) Assignees: Plant Sciences, Inc., Watsonville, CA (US); Berry R & D, Inc., Watsonville, CA (US)

( * ) Notice: Subject to any disclaimer, the term of this patent is extended or adjusted under 35 U.S.C. 154(b) by 0 days.

(21) Appl. No.: 09/708,570

(22) Filed: Nov. 9, 2000

(51) Int. Cl.[7] ..... A01H 5/00
(52) U.S. Cl. ..... Plt./209
(58) Field of Search ..... Plt./209

*Primary Examiner*—Bruce R. Campell
*Assistant Examiner*—Anne Marie Grünberg
(74) *Attorney, Agent, or Firm*—Foley & Lardner

(57) ABSTRACT

This invention relates to a new and distinct winter planted everbearing variety of strawberry plant named 'PS-2299'. The new variety is primarily adapted to the growing conditions of the central coast of California. Its strong vigorous plant with uniformly conical fruit of excellent quality particularly characterizes 'PS-2299'.

3 Drawing Sheets

LATIN NAME OF THE GENUS AND SPECIES OF THE PLANT CLAIMED

*Fragaria ananassa.*

VARIETY DENOMINATION

PS-2299.

BACKGROUND OF THE INVENTION

The present invention relates to a new and distinct everbearing strawberry variety designed as 'PS-2299'. This new variety is a result of a controlled cross of 'Selva' (U.S. Plant Pat. No. 5,266) and 'PS-144' (an unpatented Plant Sciences, Inc. selection). The variety is botanically known as *Fragaria ananassa.*

The seedling resulting from the aforementioned cross was asexually propagated by stolons in a nursery located in Lassen County, Calif., and was subsequently selected from a controlled breeding plot near Salinas, Calif. in 1994. After its selection, the new variety was further asexually propagated in Lassen County, Calif., Modoc County, Calif., and Siskiyou County, Calif. by stolons and extensively tested over the next several years in fruiting fields near Salinas, Calif. This propagation has demonstrated that the combination of traits disclosed herein as characterizing the new variety are fixed and remain true to type through successive generations of asexual reproduction.

BRIEF SUMMARY OF THE INVENTION

'PS-2299' is primarily adapted to the climate and growing conditions of the central coast of California. This region provides the necessary winter temperatures required for it to produce a strong vigorous plant and to remain in fruit production from April through November. The nearby Pacfic Ocean provides the needed humidity and moderate temperatures to maintain fruit quality during the winter and spring production months. The following list of traits in combination defines 'PS-2299' as a unique variety distinguishing it from other closely related commercial varieties in the region. The varieties which are believed to be the most closely related to 'PS-2299' are 'PS-592' (U.S. Plant Pat. No. 9,903) and 'PS-1150' (U.S. Plant Pat. No. 10,780).

'PS-2299' is a large vigorous plant. The average length of time from flowering to ripening is between 26 and 32 days, depending on environmental conditions. In cooler temperatures ripening time is longer, in warmer temperatures ripening time is shorter. When provided with optimum chilling in nursery propagation fields prior to being dug and artificial cold storage prior to being planted, the plant of 'PS-2299' is larger and more vigorous than the variety 'PS-1150'. The foliage of 'PS-2299' is slightly darker in color than both 'PS-592' and 'PS-1150'. The leaf in cross section of 'PS-2299' is slightly concave to slightly convex while 'PS-592' is slightly concave. The terminal leaf length to width ratio of 'PS-2299' is longer than broad while 'PS-592' is much longer than broad. The leaf blistering of 'PS-2299' is medium to strong while 'PS-1150' is medium to weak. Terminal leaflet size of 'PS-2299' is medium to large while 'PS-592' is large and 'PS-1150' is medium to small. Leaf gloss of 'PS-2299' is medium while 'PS-592' is strong and 'PS-1150' is weak. Stipule anthocyanin coloration of 'PS-2299' is strong while 'PS-1150' is absent or very weak. The petioles of 'PS-2299' are longer in length and larger in diameter than 'PS-1150'. Table 4 illustrates foliage characteristics of 'PS-2299', 'PS-592' and 'PS-1150'.

'PS-2299' is capable of long season fruit production with fruit of good size and excellent quality during the entire season when provided with optimum chilling in nursey propagation fields and artifical cold storage prior to being planted. Fruit production begins as early as late March to early April, and may continue cropping into November if rains and cold temperatures do not prevent the harvest. This is earlier with a heavier April/May crop than 'PS-1150' yet similar to 'PS-592'. 'PS-2299' season average fruit size is slightly larger than 'PS-1150' yet smaller than 'PS-592' with total yields less than 'PS-592' and slightly greater than 'PS-1150'. 'PS-2299' also produces fewer and thinner runners per plant in the fruiting fields than 'PS-592' (Table 1). The stolon anthocyanin coloration of 'PS-2299' is medium to strong while 'PS-592' is medium to weak. The stolon pubescence of 'PS-2299' is weak whie 'PS-592' is medium and 'PS-1150' is medium to strong.

The fruit of 'PS-2299' is smooth with very few longitudinal creases and very good overall appearance and gloss. See Table 3 for fruit quality performance ratings. The average soluble solid content of the fruit measured in percent Brix is 7.7, with percent Brix being an indirect measurement of the sugar content in fruit. The fruit length to width ratio of 'PS-2299' is much longer than broad while both 'PS-592' and 'PS-1150' are as long as broad to slightly longer than broad. The fruit color of 'PS-2299' is medium red while 'PS-592' is light red. Immature fruit color of 'PS-2299' is medium to light greenish white, ranging from 10Y 8.5/4 to 10Y 8/6. Flesh color of 'PS-2299' is medium red, ranging from 7.5R 4/10 to 7.5R 4/12. The attitude of the calyx segments of 'PS-2299' is typically collapsing to spreading while 'PS-592' is spreading to reflexed. The size of the calyx in relation to the fruit diameter of 'PS-2299' is much larger while both 'PS-592' and 'PS-1150' are slightly larger. The fruit flesh firmness of 'PS-2299' is firm while 'PS-592' is medium. The skin firmness of 'PS-2299' is very firm while 'PS-592' is medium firm. The fruit flavor of 'PS-2299' is less sweet as compared to 'PS-592'. Table 2 illustrates fruit characteristics of 'PS-2299', 'PS-592' and 'PS-1150'. 'PS-2299' seeds are medium yellow to medium red, ranging from 5Y 6/8 to 7.5R 3/8 with a receptacle color of white, ranging from N9.25/84.2% R to N9/78.7% R.

The total inflorescence length of 'PS-2299' is longer than 'PS-1150'. 'PS-2299' has a longer and thicker primary peduncle than 'PS-1150' while the pedicel holding the primary berry is similar in length to both 'PS-592' and 'PS-1150' yet larger in diameter than 'PS-1150'. The inflorescence position relative to the foliage for 'PS-2299' is typically held above the plant while 'PS-592' typically is held level with to beneath the foliage of the plant. Typically the inflorescence anthocyanin coloration of 'PS-2299' is moderate while 'PS-592' is light and 'PS-1150' is strong. See Table 5 for inflorescence characteristics. The flower size of 'PS-2299' is large while 'PS-1150' is medium. The petal length to width ratio of 'PS-2299' is broader than long while 'PS-592' is as long as broad and 'PS-1150' is longer than broad. See Table 6 for flower characteristics.

In comparison to the parental cultivars, the average fruit size of 'PS-2299' is smaller than both 'Selva' and 'PS-144' with comparable yields to 'Selva' and greater yields than 'PS-144'. The fruit of 'PS-2299' is more uniformly conic in shape, smoother, with fewer longitudinal creases than both 'Selva' and 'PS-144', with firmer skin, gloss, and overall appearance. The fruit color of 'PS-2299' is darker than 'Selva'. The plant vigor of 'PS-2299' is greater than 'Selva' and similar to 'PS-144'.

For identification a series of molecular markers have been determined for this new variety.

BRIEF DESCRIPTIONS OF THE DRAWINGS

The accompanying color photographs show typical specimens of the new variety at various stages of development as nearly true as it is possible to make in color reproductions:

The first photograph shows a close-up of typical field fruiting characteristics in early June of 1999 in Salinas, Calif.;

The second photograph shows typical field fruiting characteristics and plant growth in early June of 1999 in Salinas, Calif.;

The third photograph shows a close-up view of fruit harvested in mid July of 2000 from Salinas, Calif. and packed in a standard twelve dry pint crate.

DETAILED BOTANICAL DESCRIPTION

The following is a detailed description of 'PS-2299' in accordance with UPOV terminology. Unless otherwise noted, this detailed description is based on observations taken during the 1999 growing season in Salinas, Calif. These measurements and ratings were made from plants dug from a high-elevation nursery located in Siskiyou County, Calif. in October 1998 and planted in Salinas, Calif. in November 1998. Yield observations are averaged from data collected during the 1997 through 1999 growing season. The characteristics of the new variety may vary in detail, depending upon variations in environmental factors, including weather (temperature, humidity and light intensity), day length, soil type and location. 'PS-2299' has not been observed under all possible environmental conditions. Color terminology follows the Munsell Book of Colors, Munsell Color, Baltimore, Md. (1976). All colors separated by a dash connote a range of colors.

Fruit Characteristics

'PS-2299' fruit, fruit production and runner production (fruiting field) characteristics as compared to those of 'PS-592' and 'PS-1150'.

TABLE 1

1997–1999 average market fruit yield, fruit size and runner production characteristics from plants harvested from April through November, 1997–1999 of 'PS-2299' dug from a high elevation nursery (Tule Lake, California) on October 10–13 and planted 21–24 days later and compared with 'PS-592' and 'PS-1150' in Salinas, California.

| Cultivar | April/May GM/PL | Total Yield GM/PL | Average Fruit Size GRM | Average Runners/PL |
|---|---|---|---|---|
| 'PS-2299' | 275 | 1304 | 21.4 | 1.3 |
| 'PS-592' | 267 | 1665 | 25.1 | 3.1 |
| 'PS-1150' | 131 | 1200 | 20.3 | 0.3 |

TABLE 2

Comparison of primary fruit characteristics of 'PS-2299', 'PS-592' and 'PS-1150' from Salinas, California, June 12, 1999.

| Character | 'PS-2299' | 'PS-592' | 'PS-1150' |
|---|---|---|---|
| Munsell Color | 7.5R 3/10–4/10 | 7.5R 3/12–4/12 | 7.5R 4/10–3/8 |
| Fruit Length mean (cm) | 5.3 | 4.6 | 4.4 |
| range | 4.6–5.9 | 4.1–5.5 | 3.6–5.0 |
| Fruit Width mean (cm)* | 4.3 | 4.6 | 4.3 |
| range | 3.9–4.8 | 4.0–5.1 | 3.5–4.9 |
| Fruit Length/Width Ratio | 1.22 | 1.00 | 1.02 |
| Calyx Diameter mean | 6.5 | 6.0 | 5.2 |
| (cm) range | 5.6–7.0 | 5.0–6.8 | 4.6–6.0 |

*Width is measured across the widest part of the berry, typically across the shoulders

TABLE 3

Comparison of 1997–1999 fruit quality of 'PS-2299', 'PS-592' and 'PS-1150' from Salinas, California.*

| Character | 'PS-2299' | 'PS-592' | 'PS-1150' |
|---|---|---|---|
| Skin Firmness | 8.4 | 7.6 | 8.2 |
| Fruit Appearance | 7.8 | 8.0 | 8.2 |
| Fruit Gloss | 8.2 | 8.1 | 8.2 |

*Results are averaged from 3 years of replicated holding test performed from April through September 1997, 1998 and 1999. Ratings are based on a scale from 1–10; the higher the rating, the stronger and the more attractive and glossy the berry.

Fruit characteristics are taken from secondary fruit on a first year planting where appropriate.

Fruit:

*Ratio of length/width.*—Much longer than broad.
*Size.*—Medium.
*Predominant shape.*—Conical and Cordiform.
*Difference in shapes between primary and secondary fruits.*—Slight.
*Band without acheness.*—Absent or very narrow.
*Unevenness of surface.*—Absent or very weak.
*Color.*—Red.
*Evenness of color.*—Even.
*Glossiness.*—Strong.
*Insertion of acheness.*—Level with surface.
*Insertion of calyx.*—In basin.
*Attitude of the calyx segments.*—Collapsing and spreading.
*Size of calyx in relation to fruit diameter.*—Much larger.
*Adherence of calyx (when fully ripe).*—Strong.
*Firmness of skin.*—Firm to very firm.
*Firmness of flesh.*—Firm.
*Color of flesh.*—Medium red.
*Hollow center.*—Weakly expressed.
*Distribution of red color of flesh.*—Marginal and central.
*Time of flowering (50% of plants at first flower).*—Early.
*Time of ripening (50% of plants with ripe fruit).*—Early.
*Type of bearing.*—Fully remontant.

Plant Characteristics

Plant characteristics are based upon plants planted with optimum field chilling and subsequent optimum artificial cold storage.

Plant:

*Size.*—Average plant height 27.8 cm; average plant spread 34.2 cm.
*Habit.*—Globose.
*Density.*—Medium.
*Vigor.*—Strong.

Stolons:

*Number.*—1.3 runners per plant.
*Anthocyanin coloration.*—Medium to strong.
*Thickness.*—Thin to medium.
*Pubescence.*—Weak.

Foliage Characteristics

'PS-2299' foliage characteristics as compared to those of 'PS-592' and 'PS-1150'.

TABLE 4

Comparison of leaf characteristics of 'PS-2299', 'PS-592' and 'PS-1150' from Salinas, California, July 6, 1999.

| Character | 'PS-2299' | 'PS-592' | 'PS-1150' |
|---|---|---|---|
| Munsell Color (upper surface) | 7.5GY 2/4–3/4 | 7.5GY 4/4–3/4 | 7.5GY 3/4–4/4 |
| Terminal Leaflet Length | 7.9 | 8.5 | 7.3 |
| mean (cm) range | 7.4–8.7 | 7.9–9.1 | 6.7–8.1 |
| Terminal Leaflet Width | 7.3 | 7.1 | 6.5 |
| mean (cm) range | 5.6–8.8 | 6.6–7.7 | 6.0–7.2 |
| Terminal Leaflet ratio (L/W) | 1.08 | 1.20 | 1.12 |
| Petiol Length mean (cm) | 19.8 | 21.8 | 17.1 |
| range | 16.6–24.0 | 17.5–26.4 | 14.0–21.3 |
| Petiole Width mean (mm) | 3.9 | 4.2 | 3.4 |
| range | 3.4–3.5 | 3.2–4.8 | 2.9–4.0 |
| Petiolule Length mean | 9.5 | 6.5 | 7.3 |
| (mm) range | 5.0–15.0 | 5.0–15.0 | 5–10 |
| Serrations/Leaf | 25.9 | 19.2 | 22.3 |
| Serration Depth mean | 4.4 | 5.8 | 4.4 |
| (mm) range | 2–7 | 3–10 | 3–6 |

Foliage characteristics are taken from a fully mature tri-foliate during mid season.

Foliage:

*Color of upper surface.*—Medium green to dark green.
*Shape in cross section.*—Slightly concave to slightly convex.
*Blistering.*—Medium to strong.
*Glossiness.*—Medium.

Terminal leaflet:

*Size.*—Medium to large.
*Length/width ratio.*—Longer than broad.
*Shape of base.*—Obtuse.
*Shape of incision of margins.*—Serrate.
*Depth of serration.*—Medium to shallow.

Petiole:

*Pubescence.*—Sparse.
*Anthocyanin coloration of stipule.*—Strong.
*Attitude of hairs.*—Strongly outward.
*Length.*—Medium to long.
*Thickness.*—Medium.

Flowers and Inflorescences

'PS-2299' inflorescence and flower characteristics as compared to those of 'PS-592' and 'PS-1150'.

TABLE 5

Comparison of inflorescence characteristics of 'PS-2299', 'PS-592' and 'PS-1150' from Salinas, California, June 10, 1999.

| Character | 'PS-2299' | 'PS-592' | 'PS-1150' |
|---|---|---|---|
| Inflorescence Length | 30.9* | 30.8 | 23.7 |
| mean (cm) range | 25.5–35.0 | 25.0–34.0 | 21.6–28.2 |
| Primary Peduncle Length | 13.0 | 11.4 | 6.8 |
| mean (cm) range | 7.5–15.5 | 4.0–17.0 | 4.0–10.0 |
| Primary Peduncle Width | 5.4 | 6.3 | 4.9 |

TABLE 5-continued

Comparison of inflorescence characteristics of 'PS-2299', 'PS-592' and 'PS-1150' from Salinas, California, June 10, 1999.

| Character | 'PS-2299' | 'PS-592' | 'PS-1150' |
|---|---|---|---|
| mean (mm) range | 4.6–6.0 | 4.8–7.7 | 3.3–5.8 |
| Primary Pedicel Length | 10.7 | 9.9 | 10.9 |
| mean (cm) range | 7.8–12.5 | 5.8–14.5 | 8.0–13.5 |
| Primary Pedicel Width | 3.2 | 3.2 | 2.7 |
| mean (mm) range | 2.5–3.8 | 2.6–3.8 | 2.1–3.2 |

*as measured from the base of the primary peduncle where it attaches to the crown of the plant to the furthest berry

TABLE 6

Comparison of flower characteristics of 'PS-2292', 'PS-592' and 'PS-1150' from Salinas, California, July 6, 1999.

| Character | 'PS-2299' | 'PS-592' | 'PS-1150' |
|---|---|---|---|
| Primary Flower Diameter | 3.8 | 3.8 | 3.7 |
| mean (cm) range | 3.8–4.4 | 3.0–4.9 | 2.6–4.6 |
| Primary Petal Length | 12.2 | 13.4 | 12.3 |
| mean (mm) range | 10–14 | 12–15 | 10–15 |
| Primary Petal Width | 13.0 | 13.0 | 10.7 |
| mean (mm) range | 11–14 | 11–15 | 6–14 |
| Primary Petal L/W Ratio | 0.90 | 1.03 | 1.10 |
| Petals/Primary Flower | 7.3 | 7.2 | 9.1 |

Inflorescence characteristics are taken from a fully mature plant during mid season. Flower characteristics are taken from a secondary flower during mid season at full maturity:

Inflorescence:

*Position relative to foliage.*—Above.

*Overall length.*—Long.

*Primary peduncle length.*—Medium to long.

*Primary peduncle width.*—Medium.

*Primary pedicel length.*—Medium to long.

*Primary pedicel width.*—Thick.

*Pubescence.*—Strong.

*Anthocyanins.*—Moderate.

Flowers:

*Color.*—White.

*Size.*—Large.

*Size of calyx relative to corolla.*—Large.

*Relative position of petals* (*observed only on flowers with 5 or 6 petals*).—Overlapping.

*Length/width ratio.*—Broader than long.

Pest Reactions

This new variety may not be resistant to any of the known insects, diseases or viruses common in California. It is known to be moderately susceptible to the two-spotted spider mite, aphid and flower thrips. It is also known to be moderately susceptible to grey fruit mold and powdery mildew. The susceptibility of the new variety to any of the virus complexes of California has not been determined.

We claim:

1. A new and distinct strawberry plant as herein described and illustrated by the characteristics set forth above.

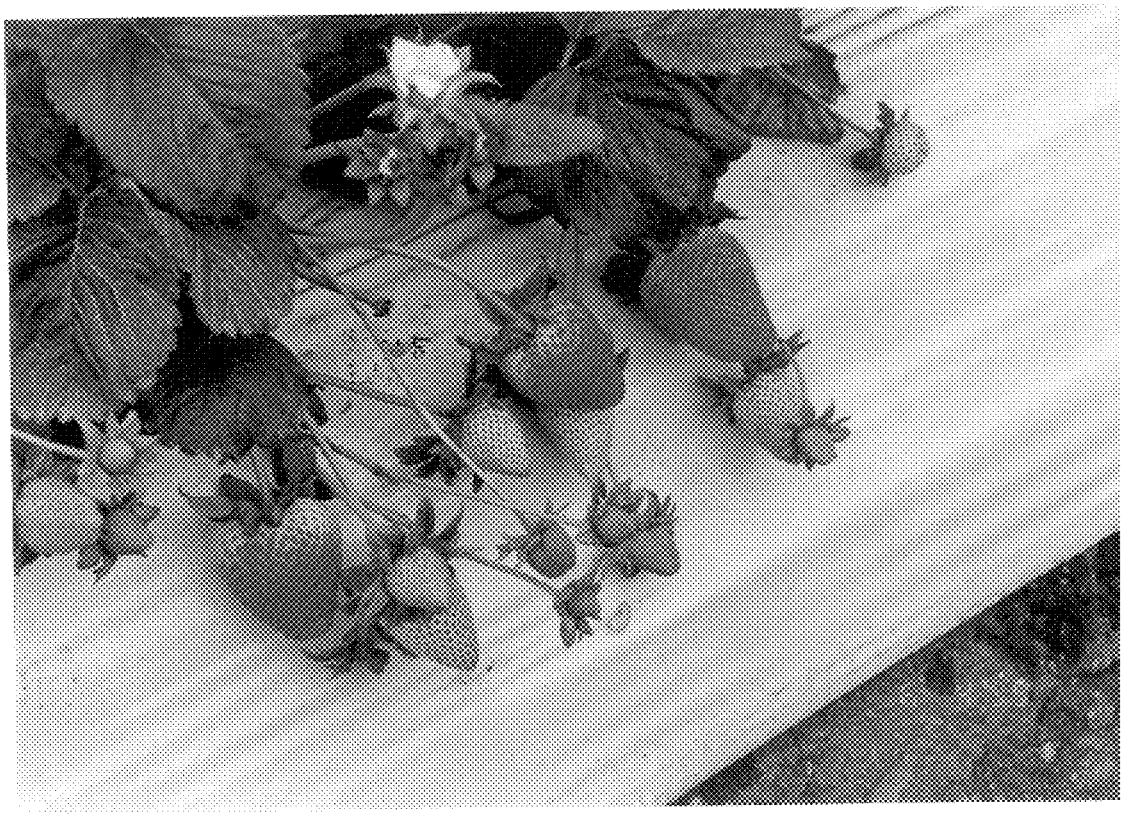

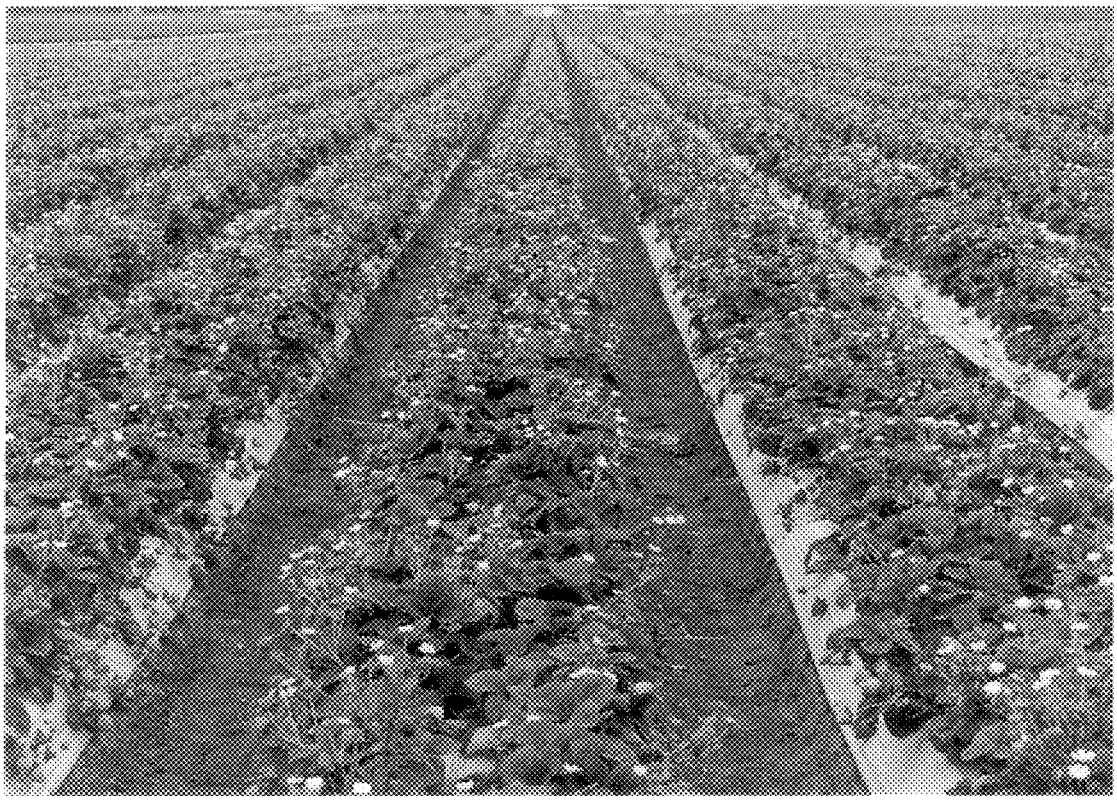

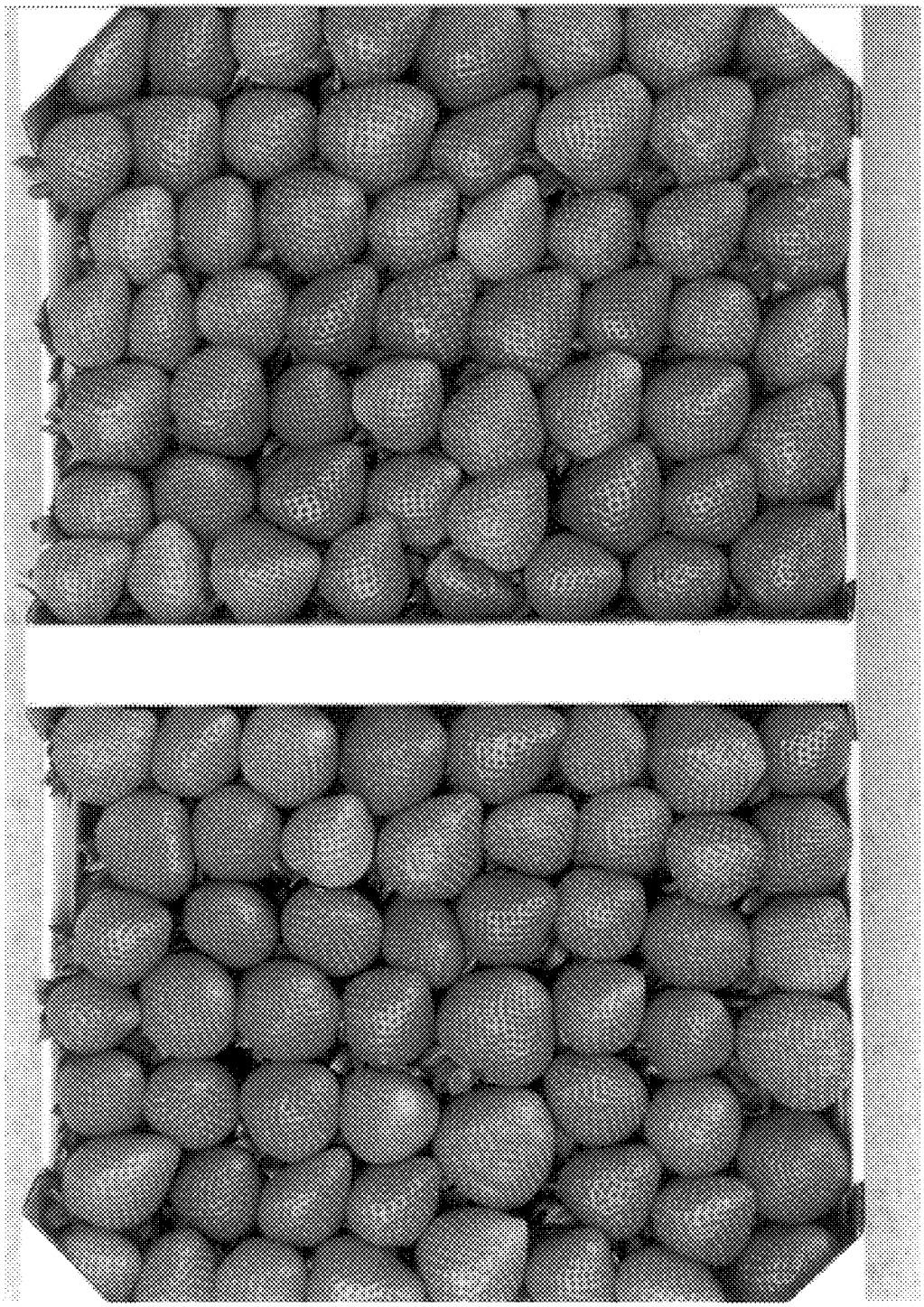

* * * * *